United States Patent [19]

Goodson, Jr. et al.

[11] Patent Number: 6,090,850
[45] Date of Patent: Jul. 18, 2000

[54] NAPHTHYL GLYOXAMIDES AS SPLA$_2$ INHIBITORS

[75] Inventors: Theodore Goodson, Jr.; David K. Herron, both of Indianapolis, Ind.

[73] Assignee: Eli Lilly and Company, Indianapolis, Ind.

[21] Appl. No.: 09/091,079

[22] PCT Filed: Dec. 9, 1996

[86] PCT No.: PCT/US96/19529

§ 371 Date: Jun. 9, 1998

§ 102(e) Date: Jun. 9, 1998

[87] PCT Pub. No.: WO97/21716

PCT Pub. Date: Jun. 19, 1997

[30] Foreign Application Priority Data

Feb. 5, 1996 [GB] United Kingdom ............... 9602268

[51] Int. Cl.$^7$ ................ A01N 41/04; A01N 37/10; A01N 31/08; C07F 9/22; C07C 229/28

[52] U.S. Cl. ............... 514/563; 514/119; 514/709; 562/15; 562/42; 562/451; 562/455

[58] Field of Search ............... 514/119, 563, 514/709; 562/15, 42, 451, 455

[56] References Cited

U.S. PATENT DOCUMENTS 5,436,369  7/1995  Bronson et al. ............... 562/495

FOREIGN PATENT DOCUMENTS 0447 285  9/1991  European Pat. Off. .

OTHER PUBLICATIONS

Database CAPLUS on STN, Acc. No. 1985:504763, Steglich et al., 'Fungal Pigments. Part 47. Easy access to the naphthol[1,8–bc]pryrandione system.' Angew. Chem. (1985), 97(8), p716–717 (abstract).

Beaton, Haydn G. et al.: "Discovery of New Non–Phospholipid Inhibitors of the Secretory Phospholipases AS" J. Med. Chem. (1994), 37(5), 557–9 CODEN: JMCMAR;ISSN: 0022–2623, 1994, XP000617261.

Chemical Abstracts, vol. 55, No. 22, 1961 Columbus, Ohio, US; abstract No. 22248i J. Moszew Et Al.: "Synthetic plant growth regulators. VI. Benzyl derivatives of 1–naphtylacetic acid as plant regulators" XP002028477 *abstract; example VIII* & Rocznicki Chem., vol. 34, 1960, pp. 1387–1396.

*Primary Examiner*—Johann Richter
*Assistant Examiner*—Brian J. Davis
*Attorney, Agent, or Firm*—Arleen Palmberg

[57] ABSTRACT

A class of novel naphthyl glyoxamide compounds of formula (I) is disclosed together with a process for making the novel naphthyl glyoxamide compounds and the use of such compounds for inhibiting sPLA$_2$ mediated release of fatty acids for treatment of conditions such as septic shock.

8 Claims, No Drawings

NAPHTHYL GLYOXAMIDES AS SPLA$_2$ INHIBITORS

This application is a 371 of PCT/US96/19529 filed Dec. 9, 1996, which also claims priority from U.S. provisional application Ser. No. 60/008,557 filed Dec. 13, 1995.

BACKGROUND OF THE INVENTION

This invention relates to novel naphthyl glyoxamides useful for inhibiting sPLA$_2$ mediated release of fatty acids for conditions such as septic shock. These compounds are also known as naphthyl oxyalamides or naphthyl oxamides.

The structure and physical properties of human non-pancreatic secretory phospholipase A$_2$ (hereinafter called, "sPLA$_2$") has been thoroughly described in two articles, namely, "Cloning and Recombinant Expression of Phospholipase A$_2$ Present in Rheumatoid Arthritic Synovial Fluid" by Seilhamer, Jeffrey J.; Pruzanski, Waldemar; Vadas Peter; Plant, Shelley; Miller, Judy A.; Kloss, Jean; and Johnson, Lorin K.; *The Journal of Biological Chemistry*, Vol. 264, No. 10, Issue of Apr. 5, 1989; pp. 5335–5338, and "Structure and Properties of a Human Non-pancreatic Phospholipase A$_2$" by Kramer, Ruth M.; Hession, Catherine; Johansen, Berit; Hayes, Gretchen; McGray, Paula; Chow, E. Pingchang; Tizard, Richard; and Pepinsky, R. Blake; *The Journal of Biological Chemistry*, Vol. 264, No. 10, Issue of Apr. 5, 1989; pp. 5768–5775, the disclosures of which are incorporated herein by reference.

It is believed that sPLA$_2$ is a rate limiting enzyme in the arachidonic acid cascade which hydrolyzes membrane phospholipids. Thus, it is important to develop compounds which inhibit sPLA$_2$ mediated release of fatty acids (e.g., arachidonic acid). Such compounds would be of value in general treatment of conditions induced and/or maintained by over-production of sPLA$_2$; such as septic shock, adult respiratory distress syndrome, pancreatitis, trauma, bronchial asthma, allergic rhinitis, rheumatoid arthritis, and etc.

The Communication to the Editor by Hayden G. Beaton et al., Journal of Medicinal Chemistry, 1994, Vol. 37, No. 5, describes various novel (naphthylthio)methyl analogs of non-phospholipid sPLA$_2$ inhibitors.

It is desirable to develop new compounds and treatments for sPLA$_2$ induced diseases.

This invention is a novel use of compounds known as naphthyl glyoxamide compounds as depicted in the general formula I:

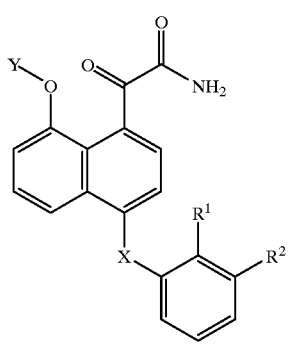

(I)

where R$^1$, R$^2$, X and Y are as defined below.

These naphthyl glyoxamide compounds are effective in inhibiting human sPLA$_2$ mediated release of fatty acids.

This invention is also a novel class of naphthyl glyoxamides having potent and selective effectiveness as inhibitors of human sPLA$_2$.

This invention is also a process for preparing the novel class of naphthyl glyoxamide compounds.

This invention is also a pharmaceutical composition containing a naphthyl glyoxamide compound.

This invention is also a method of preventing and treating septic shock, adult respiratory distress syndrome, pancreatitis, trauma, bronchial asthma, allergic rhinitis, rheumatoid arthritis, and related diseases by contact with a therapeutically effective amount of the naphthyl glyoxamide.

Definitions:

The napthyl glyoxamides of the invention employ certain defining terms as follows:

The term, "alkyl" by itself or as part of another substituent means, unless otherwise defined, a straight or branched chain monovalent hydrocarbon radical such as methyl, ethyl, n-propyl, isopropyl, n-butyl, tertiary butyl, isobutyl, sec-butyl, n-pentyl, and n-hexyl.

The term, "alkenyl" employed alone or in combination with other terms means a straight chain or branched monovalent hydrocarbon group having the stated number range of carbon atoms, and typified by groups such as vinyl, propenyl, crotonyl, isopentenyl, and various butenyl isomers.

The term "C$_2$–C$_6$ alkynyl" refers to straight and branched chains of 2 to 6 carbon atoms, both inclusive, having a triple bond. As such, the term includes acetylene, propyne, 1-butyne, 2-butyne, 1-pentyne, 2-pentyne, 3-methyl-1-butyne, 1-hexyne, 2-hexyne, 3-hexyne and the like.

The term, "halo" means fluoro, chloro, bromo, or iodo.

The term, "non-interfering substituent", refers to radicals suitable for substitution on the phenyl ring attached to the naphthalene ring. Illustrative non-interfering radicals are C$_1$–C$_6$ alkyl, C$_2$–C$_6$ alkenyl, C$_2$–C$_6$ alkynyl, C$_7$–C$_{12}$ aralkyl, C$_7$–C$_{12}$ alkaryl, C$_3$–C$_8$ cycloalkyl, C$_3$–C$_8$ cycloalkenyl, phenyl, toluyl, xylenyl, biphenyl, C$_1$–C$_6$ alkoxy, C$_1$–C$_6$ alkenyloxy, C$_1$–C$_6$ alkynyloxy, C$_2$–C$_{12}$ alkoxyalkyl, C$_2$–C$_{12}$ alkoxyalkyloxy, C$_2$–C$_{12}$ alkylcarbonyl, C$_2$–C$_{12}$ alkylcarbonylamino, C$_2$–C$_{12}$ alkoxyamino, C$_2$–C$_{12}$ alkoxyaminocarbonyl, C$_1$–C$_{12}$ alkylamino, C$_1$–C$_6$ alkylthio, C$_2$–C$_{12}$ alkylthiocarbonyl, C$_1$–C$_6$ alkylsulfinyl, C$_1$–C$_6$ alkylsulfonyl, C$_1$–C$_6$ haloalkoxy, C$_1$–C$_6$ haloalkylsulfonyl, C$_1$–C$_6$ haloalkyl, C$_1$–C$_6$ hydroxyalkyl, —C(O)O(C$_1$–C$_6$ alkyl), —(CH$_2$)$_n$—O—(C$_1$–C$_6$ alkyl), benzyloxy, phenoxy, phenylthio, —(CONHSO$_2$R), —CHO, amino, amidino, bromo, carbamyl, carboxyl, ethoxycarbonyl, —(CH$_2$)$_n$—CO$_2$H, chloro, cyano, cyanoguanidinyl, fluoro, guanidino, hydrazide, hydrazino, hydrazido, hydroxy, hydroxyamino, iodo, nitro, phosphono, —SO$_3$H, thioacetal, thiocarbonyl, and C$_1$–C$_6$ carbonyl; where n is from 1 to 8.

Compounds of the Invention

Compounds of the invention are represented by formula I

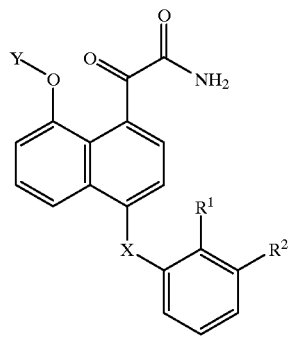

wherein:
- $R^1$ and $R^2$ are each independently hydrogen or a non-interfering substituent with the proviso that at least one of $R^1$ or $R^2$ must be hydrogen;
- X is —$CH_2$— or —O—; and
- Y is $(CH_2)_n Z$ where n is a number from 1–3 and Z is an acid group selected from the group consisting of —$CO_2H$, —$SO_3H$ or —$PO(OH)_2$.

Preferred Compounds

A preferred subclass of compounds of formula I are those wherein $R^1$ and $R^2$ are hydrogen or phenyl.

Another preferred subclass of compounds of formula I are those wherein Y is $(CH_2)_n Z$ where n is 1.

More particularly preferred are compounds wherein $R^1$ and $R^2$ are hydrogen or phenyl, X is oxygen or —$CH_2$— and Y is —$CH_2CO_2H$.

Specific preferred compounds and all pharmaceutically acceptable salts, solvates and prodrug derivatives thereof which are illustrative of the compounds of the invention include the following:

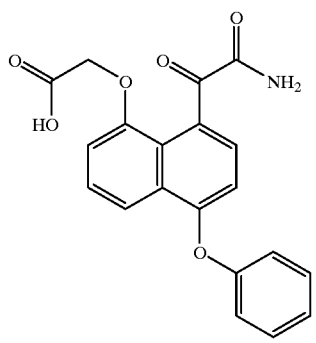

The salts of the above naphthyl glyoxamide compounds are an additional aspect of the invention. In those instances where the compounds of the invention possess acidic or basic functional groups various salts may be formed which are more water soluble and physiologically suitable than the parent compound. Representative pharmaceutically acceptable salts, include but are not limited to, the alkali and alkaline earth salts such as lithium, sodium, potassium, calcium, magnesium, aluminum and the like. Salts are conveniently prepared from the free acid by treating the acid in solution with a base or by exposing the acid to an ion exchange resin.

Included within the definition of pharmaceutically acceptable salts are the relatively non-toxic, inorganic and organic base addition salts of compounds of the present invention, for example, ammonium, quaternary ammonium, and amine cations, derived from nitrogenous bases of sufficient basicity to form salts with the compounds of this invention (see, for example, S. M. Berge, et al., "Pharmaceutical Salts," *J. Phar. Sci.*, 66: 1–19 (1977)). Moreover, the basic group(s) of the compound of the invention may be reacted with suitable organic or inorganic acids to form salts such as acetate, benzenesulfonate, benzoate, bicarbonate, bisulfate, bitartrate, borate, bromide, camsylate, carbonate, chloride, clavulanate, citrate, chloride, edetate, edisylate, estolate, esylate, fluoride, fumarate, gluceptate, gluconate, glutamate, glycolylarsanilate, hexylresorcinate, bromide, chloride, hydroxynaphthoate, iodide, isothionate, lactate, lactobionate, laurate, malate, malseate, mandelate, mesylate, methylbromide, methylnitrate, methylsulfate, mucate, napsylate, nitrate, oleate, oxalate, palmitate, pantothenate, phosphate, polygalacturonate, salicylate, stearate, subacetate, succinate, tannate, tartrate, tosylate, trifluoroacetate, trifluoromethane sulfonate, and valerate.

Prodrugs are derivatives of the compounds of the invention which have chemically or metabolically cleavable groups and become by solvolysis or under physiological conditions the compounds of the invention which are pharmaceutically active in vivo. The prodrug derivative form often offers advantages of solubility, tissue compatibility, or delayed release in a mammalian organism (see, Bundgard, H., *Design of Prodrugs*, pp. 7–9, 21–24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine simple aliphatic or aromatic esters derived from acidic groups pendent on the compounds of this invention are preferred prodrugs. In some cases it is desirable to prepare double ester type prodrugs such as (acyloxy) alkyl esters or ((alkoxycarbonyl)oxy)alkyl esters.

Synthesis Methods

Compounds of formula I where X is oxygen can be prepared by the following reaction Scheme I.

Scheme I

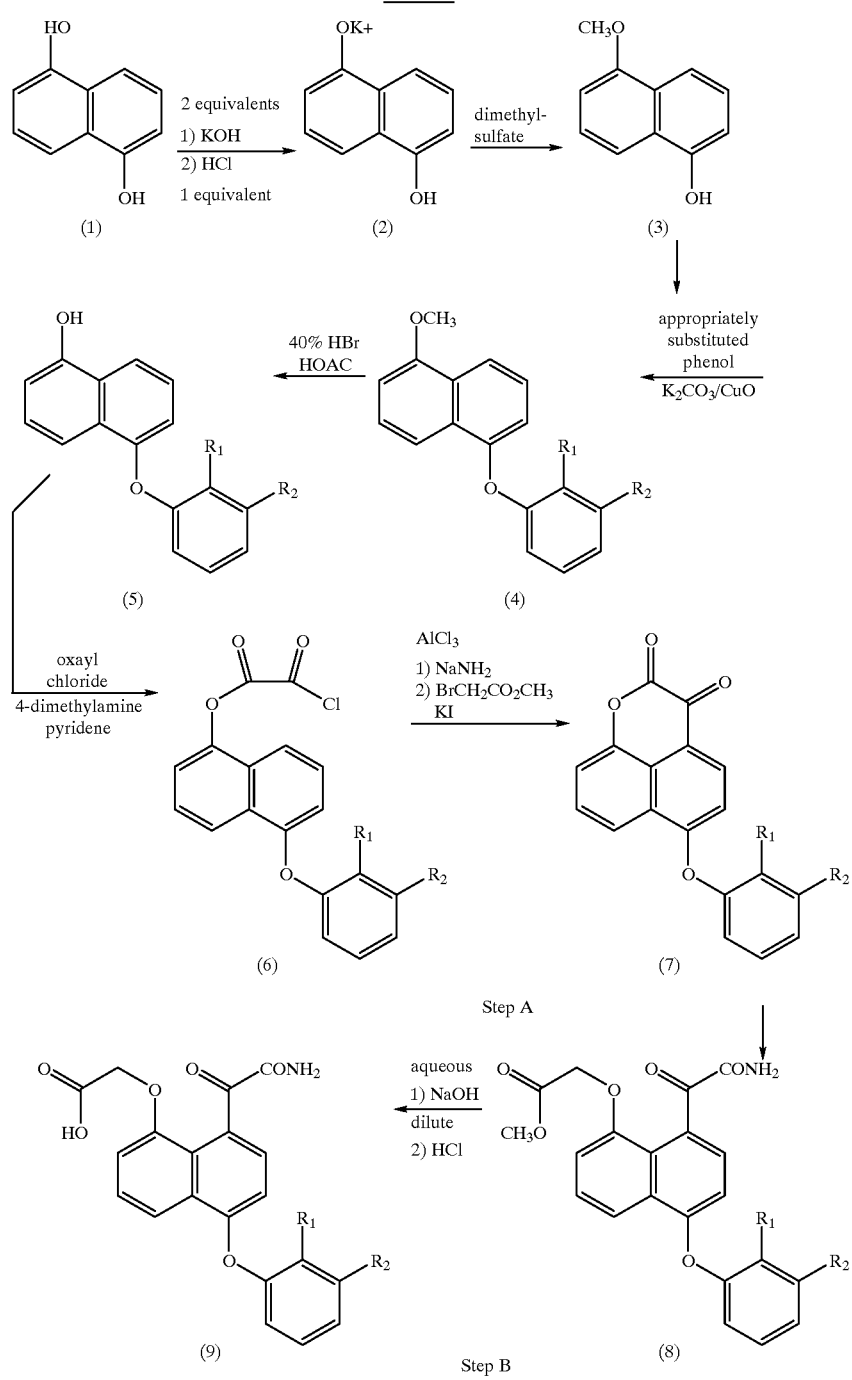

In the above depicted reaction scheme, the 1, 5-dihydroxy napthalene starting material (1) is dispersed in water and then treated with 2 equivalents of potassium hydroxide. The resultant solution is chilled in an ice bath and one equivalent of a strong mineral acid, such as hydrochloric acid, is added to produce the potassium salt (2).

Alkylation of the radical (2) can then be accomplished by treatment with a methylating agent such as dimethyl sulfate to prepare the ether (3).

Preparation of (4) is achieved by reacting the ether (3) with an appropriately substituted phenol in an Ullman-type reaction using potassium carbonate and cupric oxide.

De-methylation of (4) can be accomplished by treating (4) with a 40% HBr/HOAC solution at reflux in a protic polar solvent such as acetic acid, to prepare (5).

Reflux of compound (5) with oxalyl chloride and 4-demethylamino pyridine, in an alkylhalide solvent such as methylene chloride, prepares the oxalyl chloride (6).

Internal cyclization of (6) can be achieved under Friedel-Crafts condition using aluminum chloride or other similar metal halide as the catalyst. The reaction can be conveniently conducted in an alkyl halide solvent, such as 1, 2-dichloro ethane.

Alkylation and hydrolysis of the cyclized compound (7) can be achieved by reacting (7) with an alkaliamide base, such as sodium amide, followed by treatment with an alkylating agent, such as methyl bromoacetate, using potassium iodide as a catalyst.

Finally, the acid (9) is achieved by treating the ester (8) with an alkali base, such as aqueous sodium hydroxide, followed by treatment with a dilute aqueous mineral acid such as hydrochloric acid The acid compound (9) is then extracted with an organic solvent such as ethyl acetate.

The final product (9) can be purified using standard recrystallization procedures in a suitable organic solvent such as methylene chloride/hexane.

Compounds of formula I where X is methylene can be prepared as shown in the following Scheme II

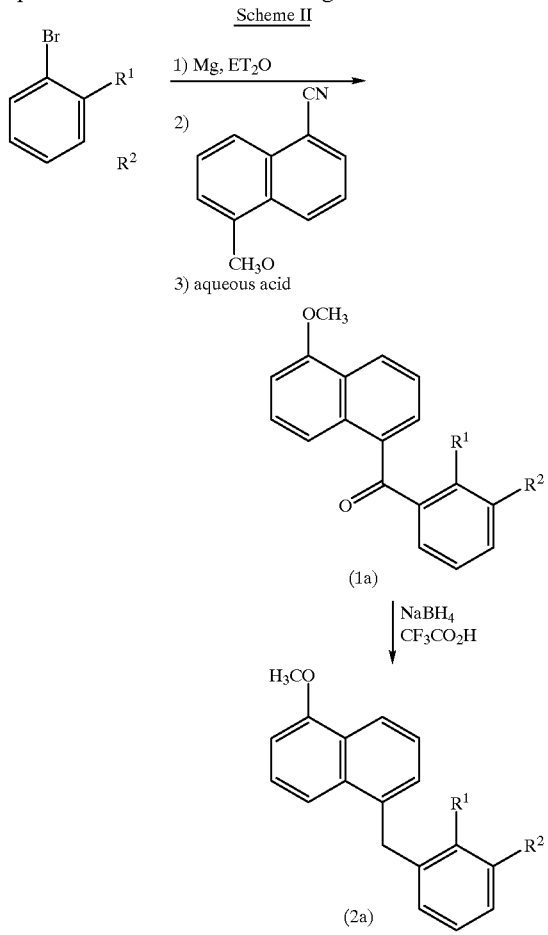

Using an appropriately substituted phenyl bromide, a Grignard reagent is prepared. The phenyl Grignard is then reacted with 4-methoxy naphthylnitrile and the resultant compound is hydrolyzed with a dilute acid such as hydrochloric acid to form the benzoyl naphthylene compound (1a).

Reduction of (1a) to form compound (2a) is accomplished by treatment with a reducing agent such as sodium borohydride. The reaction is conducted in a solvent-catalyst such as trifluoroacetic acid and initiated in an ice bath which is allowed to warm to room temperature as the reaction proceeds.

The desired naphthyl glyoxamide may then be prepared from (2a) according to the procedure in Scheme I starting with the chloromethylation step.

It will be readily appreciated by a person skilled in the art that the substituted benzyl bromide, substituted phenol and substituted naphthylnitrile compounds of Schemes I and II are either commercially available or can be readily prepared by known techniques from commercially available starting materials.

All other reactants used to prepare the compounds in the instant invention are commercially available.

Process of the Invention

The process of the present invention provides a method for synthesizing novel compounds of formula I

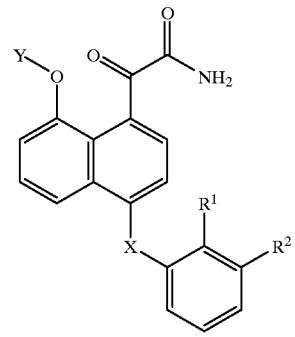

wherein:

X is —O— or —CH$_2$— which comprises reacting a compound of the formula III

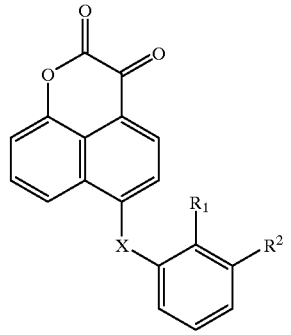

wherein X, R$^1$ and R$^2$ are as defined above, with an aklaliamide base;

alkylating with an alkylating agent to form a compound of the formula II

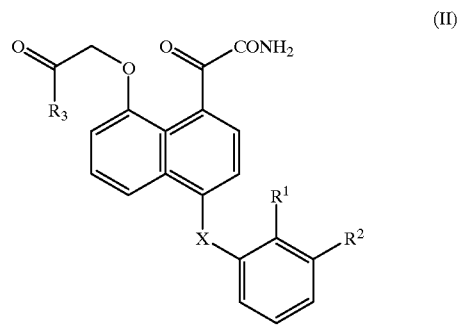

where R$^1$, R$^2$ and X are as defined above and R$^3$ is C$_1$–C$_4$ alkyl and; hydrolyzing the compound of formula II.

The process of the invention is illustrated in Scheme I, steps A and B.

According to the process of the present invention, the α-ketolactone starting material (compound III) is dissolved in an aprotic polar solvent, preferably dimethylformamide (DMF). Other suitable aproctic solvents include tetrahydrofuran (THF), dimethyl sulfoxide (DMSO) and the like. The amount of solvent used should be sufficient to ensure that all compounds stay in solution until the desired reaction is complete. The solution is chilled in an ice bath to from about −10° C. to about −30° C., preferably −20° C.

After the starting material has been dissolved, an aklaliamide base, such as sodium amide, is added to the reaction mixture and the reaction is allowed to proceed, with stirring for about 30 minutes to an hour, preferably an hour. Preferably one mole of amide per mole of starting material III is employed.

A mole of an alkylating agent, such as methylbromoacetate, per mole of starting material is added to the reaction mixture, along with a small amount of a catalyst, preferably potassium iodide to prepare the ester II. The reaction is allowed to proceed another 30 minutes to an hour, preferably for an additional hour, while maintaining the temperature below −10° C. in an ice bath.

Preparation of the acid I is accomplished by treating the ester III with an alkali base, such as sodium hydroxide, follower by treatment with a strong inorganic acid such as hydrochloric acid. The reaction is preferably conducted in a low molecular weight alcohol such as methanol at temperatures of from about 0° C. to about 40° C., preferably 25° C.

The following examples further illustrate the preparation of the compounds of this invention as well as the compounds used in the method of this invention. The examples are illustrative only and are not intended to limit the scope of the invention in any way.

EXAMPLE 1

Preparation of 8-carboxymethoxy-4-phenoxynaphth-1-yl glyoxamide

A. Preparation of the mono-potassium salt of the dihydroxynaphthalene

Into a 3-neck flask fitted with a mechanical stirrer and thermometer, 150 mL water, followed by 140 g potassium hydroxide was added. To the flask was added 128 g 1,5-dihydroxynapthalene under an argone atmosphere, and the mixture was stirred for 5 minutes. The mixture was cooled in an ice bath, and 105 mL of concentrated (37%) hydrochloric acid was added over 15 minutes, producing the mono-potassium salt of the dihydroxynaphthalene starting material.

B. Preparation of 1-hydroxy-5-methoxynaphthalene

The solution of the potassium salt, prepared as above, was treated with 126 g dimethyl sulfate, added dropwise so as not to exceed 30° C. The reaction was stirred for an additional 4 hours at room temperature, and maintained at 70° C. for 20 min. After cooling, the reaction mixture was filtered, and the precipitate was washed with aqueous potassium hydroxide, combining the washings with the filtrate. The combined filtrate was acidified with concentrated hydrochloric acid, and the precipitated 1-hydroxy-5-methoxynaphthalene was filtered, washed with water, and dried under vacuum at 50° C., yielding 82.2 g (59%).

M.P.: 127–8° C.

Elemental Analysis for $C_{11}H_{10}O_2$: Calculated: C, 75.84; H, 5.79; O, 18.37. Found: C, 75.58; H, 5.79; O, 18.30.

C. Preparation of 1-methoxy-5-phenoxynaphthalene

In a 3-neck flask fitted with a mechanical stirrer, 26.1 g of the 1-hydroxy-5-methoxynaphthalene prepared as above was treated with 16 ml bromobenzene, 41.4 g potassium carbonate, and 24.g of copper(I)oxide in 300 ml pyridine at reflux under argone. After 16 hours, an additional 3.2 mL of bromobenzene and 4.8 g of copper oxide were added and the reaction was continued for 4 hours. The reaction was cooled and filtered over supercel with an ethyl acetate washing. The combined filtrate was concentrated under vacuum, diluted with ethyl acetate, and shaken twice with cold dilute hydrochloric acid. The organic layer was dried over magnesium sulfate and evaporated under vacuum to an oil. The crude product was dissolved in 30 ml methylene chloride, and the resulting solution filtered and diluted with hexane to cloudiness. On cooling in the freezer, 3.98 g (11%) of crystalline 1-methoxy-5-phenoxynaphthalene was obtained.

M.P.: 65–66° C.

Elemental Analysis for $C_{17}H_{14}O_2$: Calculated: C, 81.58; H, 5.64; O, 12.78. Found: C, 80.01; H, 5.66; O, 13.47.

D. Preparation of 1-hydroxy-5-phenoxynaphthalene

Into 50 mL of glacial acetic acid, 3.7 g of 1-methoxy-5-phenoxynaphthalene prepared as above, followed by 20 mL of 40% aqueous hydrogen bromide was stirred. The mixture was heated at 95–100° C. for 16 hours. The solvent was removed under vacuum, and the residue was redissolved in ethyl acetate and washed three times with brine. The organic layer was dried over magnesium sulfate and filtered. After removing solvent, the residue was chromatographed over silica gel with a gradient elution of 0 to 30% ethyl acetate in hexane, providing 2.10 g (59%) of 1-hydroxy-5-phenoxynaphthalene.

M.P.: 82–83° C.

Elemental Analysis for C16 H12 O2: Calculated: C, 81.34; H, 5.12; O, 13.54. Found: C, 81.04; H, 5.23; O, 13.69.

E. Preparation of 5-phenoxy-1-naphthyl oxalylchloride

Into 100 mL of chloroform, 2.0 g of the 1-hydroxy-5-phenoxynaphthalene prepared as above, followed by 30 mg 4-dimethylaminopyridine (DAP) and 1.78 ml of oxalyl chloride, was dissolved. The mixture was refluxed for 16 hours, and the solvent was removed under vacuum, providing the desired oxalyl chloride intermediate, which was characterized by NMR.

F. Preparation of 5-phenoxy-8-hydroxy-naphthyl glyoxylic acid lactone

All of the oxalyl chloride as prepared above was redissolved in 75 mL methylene chloride and added dropwise over 15 minutes to 3.38 g of aluminum chloride in 75 mL methylene chloride cooled by an ice bath. The reaction mixture was stirred in ice bath for 1 hour and then allowed to warm to room temperature for 30 minutes. The reaction mixture was poured into 300 mL of 2:1 mixture of ice and concentrated hydrochloric acid with stirring. The organic layer was separated and washed with brine, dried over magnesium sulfate, and filtered. After removing solvent under vacuum, the residue was chromatographed over silica gel with a gradient of 0 to 100% ethyl acetate in hexane followed by 0 to 20% methanol in ethyl acetate, providing 1.4 g (54%) of the 1-oxalic acid intermediate as an oil. All of this intermediate was dissolved in 50 mL methylene chloride, and treated with excess oxalyl chloride and a catalytic amount of dimethylformamide (DMF) while the solution was cooled by an ice bath. After 30 minutes, the reaction was allowed to warm to room temperature for 1 hour. The solvent was removed under vacuum, providing the lactone as a solid, which gave 0.883 g (67%) of crystals from a concentrated methylene chloride solution.

M.P.: 195–6° C.

Elemental Analysis for C18 H10 O4: Calculated: C, 74.48; H, 3.47; O, 22.05. Found: C, 74.49; H, 3.56; O, 21.76.

G. Preparation of 8-carbomethoxy-4-phenoxy-naphth-yl-glyoxamide

Into 20 mL of dimethylformamide 0.290 g of the lactone prepared as above was dissolved. After providing for argone atmosphere and cooling the solution to −20° C., 0.049 g sodium amide was added in one portion, and stirring was continued for 15 minutes. To the reaction mixture, 0.118 mL methyl bromoacetate was added, and the temperature was maintained at −10° C. for 1 hour and then at 0° C. for 1 hour. The reaction mixture was poured into dilute, cold brine containing some hydrochloric acid, and resulting mixture was extracted with ethyl acetate. The organic layer was washed two times with cold brine containing hydrochloric acid, dried over magnesium sulfate, and filtered. After removing solvent under vacuum, the residue was chromatographed over silica gel with a gradient elution of 0 to 80% ethyl acetate in hexane, giving 186 mg (49%) of sub-titled compound as a crystalline solid. M.P.: 103–5° C.

Elemental Analysis for $C_{21}H_{17}NO_6$: Calculated: C22.49; H, 4.52; N, 3.69. Found: C, 66.30; H, 4.45; N, 3.60.

H. Preparation of 8-carboxymethoxy-4-phenoxynaphth-1-yl glyoxamide

In 10 mL methanol, 180 mg of the methyl ester amide above was treated with 0.96 mL of 0.5N sodium hydroxide for 16 hours at room temperature. Most of the methanol was removed under vacuum, and the reaction mixture was diluted with 50 ml cold water. The mixture was extracted with ethyl acetate, and the resulting aqueous layer was acidified with dilute hydrochloric acid, producing 120 mg (69%), after drying, of title compound

M.P.: 204–6° C.

Elemental Analysis for $C_{20}H_{15}NO_6$: Calculated: C, 65.75; H, 4.14; N, 3.83. Found: C, 66.01; H, 4.03; N, 3.76.

Therapeutic Use of Naphthyl Glyoxamide

Naphthyl glyoxamide compounds described herein are believed to achieve their beneficial therapeutic action principally by direct inhibition of human $sPLA_2$, and not by acting as antagonists for arachidonic acid, nor other active agents below arachidonic acid in the arachidonic acid cascade, such as 5-lipoxygenases, cyclooxygenases, and etc.

The method of the invention for inhibiting $sPLA_2$ mediated release of fatty acids comprises contacting $sPLA_2$ with an therapeutically effective amount of naphthyl glyoxamide its salt or a prodrug derivative thereof.

The compounds of the invention may be used in a method of treating a mammal (e.g., a human) to alleviate the pathological effects of septic shock, adult respiratory distress syndrome, pancreatitis, trauma, bronchial asthma, allergic rhinitis, and rheumatoid arthritis; wherein the method comprises administrating to the mammal a naphthyl glyoxamide compound of formula I in a therapeutically effective amount. A therapeutically effective amount is an amount sufficient to inhibit $sPLA_2$ mediated release of fatty acid and to thereby inhibit or prevent the arachidonic acid cascade and its deleterious products. The therapeutic amount of compound of the invention needed to inhibit $sPLA_2$ may be readily determined by taking a sample of body fluid and assaying it for $sPLA_2$ content by conventional methods.

The specific dose of a compound administered according to this invention to obtain therapeutic or prophylactic effects will, of course, be determined by the particular circumstances surrounding the case, including, for example, the compound administered, the route of administration and the condition being treated. Typical daily doses will contain a non-toxic dosage level of from about 0.01 mg/kg to about 50 mg/kg of body weight of an active compound of this invention.

Pharmaceutical Formulations of the Invention

As previously noted the compounds of this invention are useful for inhibiting $sPLA_2$ mediated release of fatty acids such as arachidonic acid. By the term, "inhibiting" is meant the prevention or therapeutically significant reduction in release of $sPLA_2$ initiated fatty acids by the compounds of the invention. By "pharmaceutically acceptable" it is meant the carrier, diluent or excipient must be compatible with the other ingredients of the formulation and not deleterious to the recipient thereof.

Preferably the pharmaceutical formulation is in unit dosage form. The unit dosage form can be a capsule or tablet itself, or the appropriate number of any of these. The quantity of active ingredient in a unit dose of composition may be varied or adjusted from about 0.1 to about 1000 milligrams or more according to the particular treatment involved. It may be appreciated that it may be necessary to make routine variations to the dosage depending on the age and condition of the patient. The dosage will also depend on the route of administration.

The compound can be administered by a variety of routes including oral, aerosol, rectal, transdermal, subcutaneous, intravenous, intramuscular, and intranasal.

Pharmaceutical formulations of the invention are prepared by combining (e.g., mixing) a therapeutically effective amount of a naphthyl glyoxamide compound of formula I together with a pharmaceutically acceptable carrier or diluent therefor. The present pharmaceutical formulations are prepared by known procedures using well known and readily available ingredients.

In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, or can be in the form of tablets, pills, powders, lozenges, elixirs, suspensions, emulsions, solutions, syrups, aerosols (as a solid or in a liquid medium), or ointment, containing, for example, up to 10% by weight of the active compound. The compounds of the present invention are preferably formulated prior to administration.

For the pharmaceutical formulations any suitable carrier known in the art can be used. In such a formulation, the carrier may be a solid, liquid, or mixture of a solid and a liquid. Solid form formulations include powders, tablets and capsules. A solid carrier can be one or more substances which may also act as flavoring agents, lubricants, solubilisers, suspending agents, binders, tablet disintegrating agents and encapsulating material.

Tablets for oral administration may contain suitable excipients such as calcium carbonate, sodium carbonate, lactose, calcium phosphate, together with disintegrating agents, such as maize, starch, or alginic acid, and/or binding agents, for example, gelatin or acacia, and lubricating agents such as magnesium stearate, stearic acid, or talc.

In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from about 1 to about 99 weight percent of the active ingredient which is the novel compound of this invention. Suitable solid carriers are magnesium carbonate, magnesium stearate, talc, sugar lactose, pectin, dextrin, starch, gelatin, tragacanth, methyl cellulose, sodium carboxymethyl cellulose, low melting waxes, and cocoa butter.

Sterile liquid form formulations include suspensions, emulsions, syrups and elixirs.

The active ingredient can be dissolved or suspended in a pharmaceutically acceptable carrier, such as sterile water, sterile organic solvent or a mixture of both. The active ingredient can often be dissolved in a suitable organic solvent, for instance aqueous propylene glycol. Other compositions can be made by dispersing the finely divided active ingredient in aqueous starch or sodium carboxymethyl cellulose solution or in a suitable oil.

The following pharmaceutical formulations I through 8 are illustrative only and are not intended to limit the scope of the invention in any way. "Active ingredient", refers to a compound according to Formula I or a pharmaceutically acceptable salt, solvate, or prodrug thereof.

Formulation 1

Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Formulation 2

A tablet is prepared using the ingredients below:

|  | Quantity (mg/tablet) |
| --- | --- |
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg

Formulation 3

An aerosol solution is prepared containing the following components:

|  | Weight |
| --- | --- |
| Active ingredient | 0.25 |
| Ethanol | 25.75 |
| Propellant 22 (Chlorodifluoromethane) | 74.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of active ingredient, are made as follows:

| Active ingredient | 60 mg |
| --- | --- |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of active ingredient, are made as follows:

| Active ingredient | 80 mg |
| --- | --- |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 6

Suppositories, each containing 225 mg of active ingredient, are made as follows:

| Active ingredient | 225 mg |
| --- | --- |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of active ingredient per 5 ml dose, are made as follows:

| Active ingredient | 50 mg |
| --- | --- |
| Sodium carboxymethyl cellulose | 50 mg |
| Syrup | 1.25 ml |
| Benzoic acid solution | 0.10 ml |
| Flavor | q.v. |

-continued

| Color | q.v. |
|---|---|
| Purified water to total | 5 ml |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| Active ingredient | 100 mg |
|---|---|
| Isotonic saline | 1,000 ml |

The solution of the above ingredients generally is administered intravenously to a subject at a rate of 1 ml per minute.

Assay Procedures

Chromogenic Assay

The following chromogenic assay procedure was used to identify and evaluate inhibitors of recombinant human secreted phospholipase $A_2$. The assay described herein has been adapted for high volume screening using 96 well microtiter plates. A general description of this assay method is found in the article, "Analysis of Human Synovial Fluid Phospholipase $A_2$ on Short Chain Phosphatidylcholine-Mixed Micelles: Development of a Spectrophotometric Assay Suitable for a Microtiterplate Reader", by Laure J. Reynolds, Lori L. Hughes, and Edward A Dennis, *Analytical Biochemistry*, 204, pp. 190–197, 1992 (the disclosure of which is incorporated herein by reference):

Reagents:

| REACTION BUFFER - | |
|---|---|
| $CaCl_2.2H_2O$ | (1.47 g/L) |
| KCl | (7.455 g/L) |
| Bovine Serum Albumin (fatty acid free) (Sigma A-7030, product of Sigma Chemical Co. St. Louis MO, USA) | (1 g/L) |
| TRIS HCl | (3.94 g/L) |
| pH 7.5 (adjust with NaOH) | |
| ENZYME BUFFER - | |
| 0.05 NaOAc.3H$_2$O, pH 4.5 | |
| 0.2 NaCl | |
| Adjust pH to 4.5 with acetic acid | |
| DTNB - 5,5'-dithiobis-2-nitrobenzoic acid | |
| RACEMIC DIHEPTANOYL THIO - PC | |
| racemic 1,2-bis (heptanoylthio)-1,2-dideoxy-sn-glycero-3-phosphorylcholine | |
| TRITON X-100 ™ prepare at 6.249 mg/ml in reaction buffer to equal 10 uM. | |

REACTION MIXTURE

A measured volume of racemic dipheptanoyl thio PC supplied in chloroform at a concentration of 100 mg/ml is taken to dryness and redissolved in 10 millimolar TRITON X-100™ nonionic detergent aqueous solution. Reaction Buffer is added to the solution, then DTNB to give the Reaction Mixture.

The reaction mixture thus obtained contains 1 mM diheptanoly thio-PC substrate, 0.29 mm Triton X-100™ detergent, and 0.12 mm DTMB in a buffered aqueous solution at pH 7.5.

Assay Procedure:

1. Add 0.2 ml reaction mixture to all wells;
2. Add 10 ul test compound (or solvent blank) to appropriate wells, mix 20 seconds;
3. Add 50 nanograms of sPLA$_2$ (10 microliters) to appropriate wells;
4. Incubate plate at 40° C. for 30 minutes;
5. Read absorbance of wells at 405 nanometers with an automatic plate reader.

All compounds were tested in triplicate. Typically, compounds were tested at a final concentration of 5 ug/ml. Compounds were considered active when they exhibited 40% inhibition or greater compared to uninhibited control reactions when measured at 405 nanometers. Lack of color development at 405 nanometers evidenced inhibition. Compounds initially found to be active were reassayed to confirm their activity and, if sufficiently active, $IC_{50}$ values were determined. Typically, the $IC_{50}$ values (see, Table I, below) were determined by diluting test compound serially two-fold such that the final concentration in the reaction ranged from 45 ug/mL to 0.35 ug/ml. More potent inhibitors required significantly greater dilution. In all cases, % inhibition measured at 405 nanometers generated by enzyme reactions containing inhibitors relative to the uninhibited control reactions was determined. Each sample was titrated in triplicate and result values were averaged for plotting and calculation of $IC_{50}$ values. $IC_{50}$ were determined by plotting log concentration versus inhibition values in the range from 10–90% inhibition.

Results of Human Secreted Phospholipase $A_2$ Inhibition Tests

Results of Human Secreted Phospholipase $A_2$ Inhibition Tests

| Compound of Example number | Inhibition of human secreted PLA$_2$ mM IC$_{50}$ ± mean deviation (3–4 tests) |
|---|---|
| 1 | 0.69 ± 0.051 |

While the present invention has been illustrated above by certain specific embodiments, it is not intended that these specific examples should limit the scope of the invention as described in the appended claims.

What is claimed is:

1. A naphthyl glyoxamide compound or a pharmaceutically acceptable salt, solvate or prodrug derivative thereof; wherein said compound is represented by the formula I

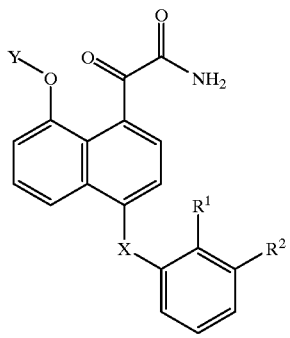

(I)

wherein:
R$^1$ and R$^2$ are each independently hydrogen or a non-interfering substituent with the proviso that at least one of R$^1$ or R$^2$ must be hydrogen;
X is —CH$_2$— or —O—; and
Y is (CH$_2$)$_n$Z where n is a number from 1–3 and Z is an acid group selected from the group consisting of —CO$_2$H, —SO$_3$H or —PO(OH)$_2$.

2. A compound of formula I wherein R$^1$ and R$^2$ are hydrogen or phenyl, Y is (CH$_2$)$_n$Z where n is 1.

3. A pharmaceutical formulation comprising a naphthyl glyoxamide as claimed in any one of claims 1 to 2 with a pharmaceutically acceptable carrier or diluent therefor.

4. A method of treating a mammal to alleviate the pathological effects of septic shock, adult respiratory distress syndrome, pancreatitis, trauma, bronchial asthma, allergic rhinitis, and rheumatoid arthritis; wherein the method comprises administration to said mammal a naphthyl glyoxamide as claimed in any one of claims 1 to 3 in an amount sufficient to inhibit sPLA$_2$ mediated release of fatty acid and to thereby inhibit or prevent the arachidonic acid cascade and its deleterious products.

5. A method of inhibiting sPLA$_2$ mediated release of fatty acids in humans comprising administering a therapeutically effective amount of a naphthyl glyoxamide as claimed in any one of claims 1 to 3.

6. A method of selectively inhibiting sPLA$_2$ mediated release of fatty acids in humans comprising administering a therapeutically effective amount of a naphthyl glyoxamide as claimed in any one of claims 1 to 3.

7. A process for preparing a compound of the formula I (I)

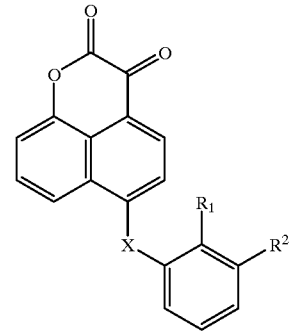

wherein:
R$^1$ and R$^2$ are each independently hydrogen or a non-interfering substituent with the proviso that at least one of R$^1$ or R$^2$ must be hydrogen;
X is —CH$_2$— or —O—; and
Y is (CH$_2$)$_n$Z where n is a number from 1–3 and Z is an acid group selected from the group consisting of CO$_2$H, —SO$_3$H or —PO(OH)$_2$, which comprises reacting a compound of the formula III (III)

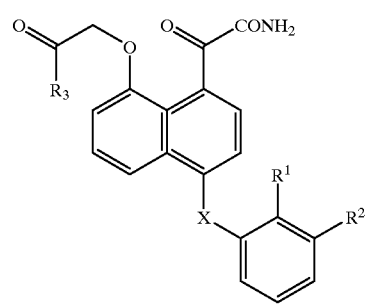

wherein X, R$^1$ and R$^2$ are as defined above, with an alkaliamide base;

alkylating with an alkylating agent to form a compound of the formula II (II)

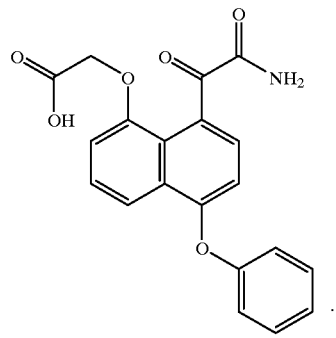

where R$^1$, R$^2$ and X are as defined above and R$^3$ is C$_1$–C$_4$ alkyl; and hydrolyzing the compound of formula II.

8. A compound of claim 1 which is

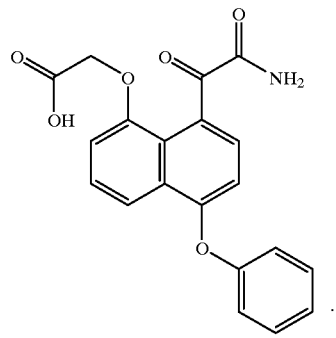

* * * * *